United States Patent [19]

Russell

[11] 4,434,963
[45] Mar. 6, 1984

[54] SLIDE CLAMP INCLUDING ELEVATION STABILIZER

[75] Inventor: Pat Russell, McHenry, Ill.

[73] Assignee: Baxter Travenol Laboratories, Inc., Deerfield, Ill.

[21] Appl. No.: 452,258

[22] Filed: Dec. 22, 1982

[51] Int. Cl.³ ............................................. F16L 55/14
[52] U.S. Cl. ......................................... 251/7; 604/250
[58] Field of Search ................ 251/4, 7; 604/34, 250; 128/346

[56] References Cited

U.S. PATENT DOCUMENTS

| | | |
|---|---|---|
| 109,382 | 11/1870 | Bulla . |
| D. 200,729 | 3/1965 | Coanda et al. . |
| D. 230,729 | 3/1974 | Zeddies . |
| D. 233,312 | 10/1974 | Lock . |
| 420,166 | 1/1890 | Phelps . |
| 420,419 | 1/1890 | Smith . |
| 927,275 | 7/1909 | Parker . |
| 2,092,400 | 9/1937 | Miller . |
| 2,503,327 | 4/1950 | Fields . |
| 2,775,240 | 12/1956 | Morrisey, Jr. et al. . |
| 2,889,848 | 6/1959 | Redmer . |
| 3,167,299 | 1/1965 | Ling . |
| 3,247,852 | 4/1966 | Schneider . |
| 3,316,935 | 5/1967 | Kaiser et al. . |
| 3,357,674 | 12/1967 | Coanda et al. . |
| 3,374,509 | 3/1968 | Logan et al. . |
| 3,555,624 | 1/1971 | Koehn . |
| 3,612,475 | 10/1971 | Dinger . |
| 4,034,773 | 7/1977 | Huggins . |
| 4,193,574 | 3/1980 | Barnes et al. ........................ 251/1 A |
| 4,248,401 | 2/1981 | Mittleman .............................. 251/7 |
| 4,307,869 | 12/1981 | Mittleman .............................. 251/7 |

Primary Examiner—Martin P. Schwadron
Assistant Examiner—Sheri Novack
Attorney, Agent, or Firm—Paul C. Flattery; John P. Kirby, Jr.; Bradford R. L. Price

[57] ABSTRACT

A slide clamp for flexible medical tubing is disclosed that includes a slot having receiving and crimping portions. A stabilizer projects into the receiving portion so that the slide clamp may be kept at any selected elevation along the tubing length when the tubing is in the receiving portion of the slide clamp. In the preferred embodiment, the slide clamp includes a channel extending from a first end of the clamp through the stabilizer, thereby forming stabilizer halves, each being capable of flexure toward and away from each other when the tubing is disposed within the receiving portion.

7 Claims, 7 Drawing Figures

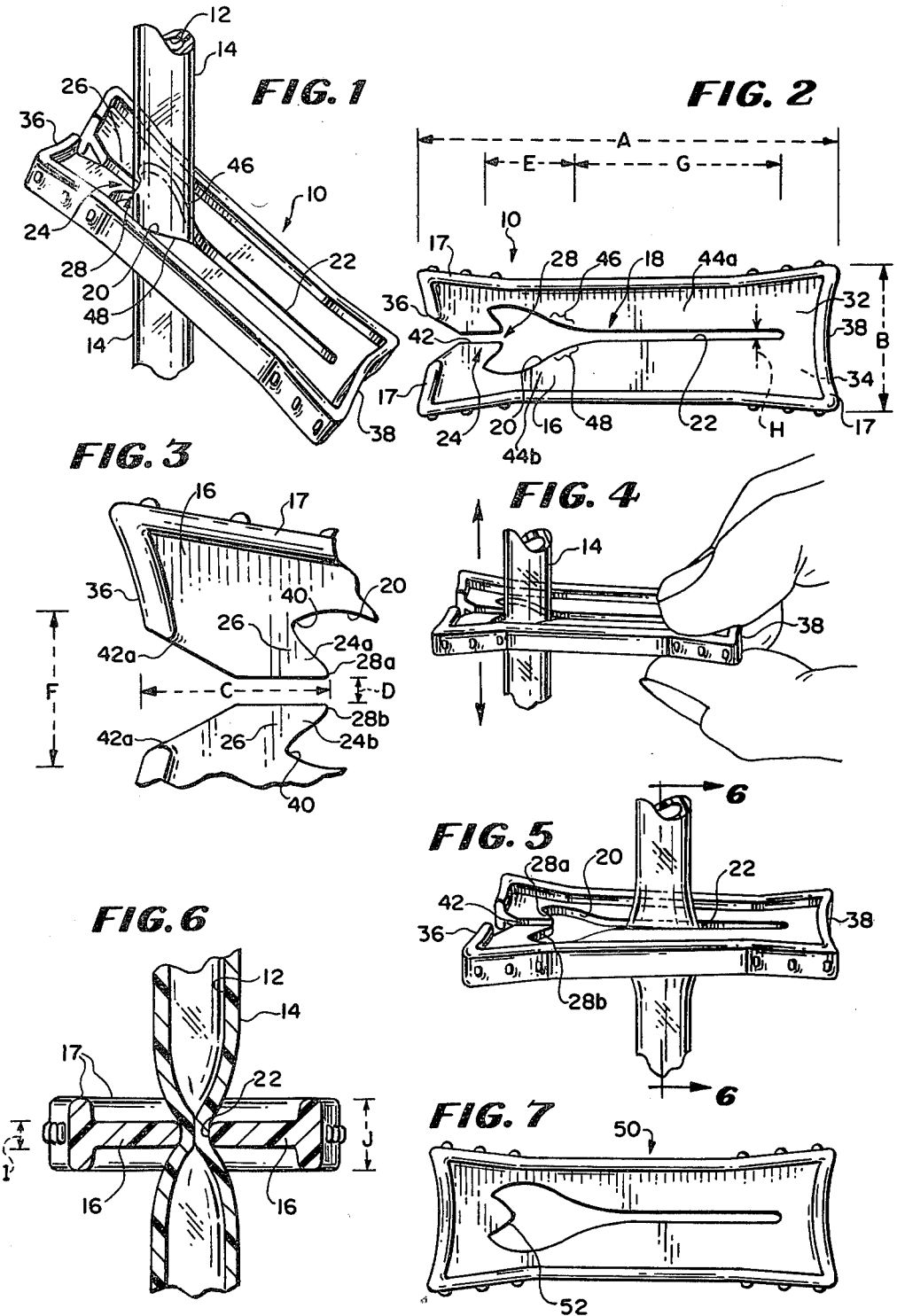

SLIDE CLAMP INCLUDING ELEVATION STABILIZER

DESCRIPTION

1. Technical Field of the Invention

The present invention relates generally to tubing clamps and more particularly to slide clamps for medical fluid tubing.

2. Background of the Invention

Slide clamps are used to control fluid flow in compressible medical tubing such as, for example, flexible polyvinyl chloride tubing commonly employed in parenteral administration sets to deliver blood, dextrose solution or other medical fluids to a patient's venous system.

Slide clamps have been used to adjust fluid flow at different flow rates between full flow and no flow, but they are principally employed as on/off clamps, i.e., to totally occlude the tubing lumen to shut off fluid flow entirely, or to allow for unrestricted fluid flow, without occluding the tubing lumen.

An example of such a slide clamp is shown in U.S. Pat. No. 4,248,401 which is incorporated by reference herein. A slide clamp as shown in FIG. 6 of that patent is sold by Travenol Laboratories, Inc. of Deerfield, Ill.

A singular disadvantage shared by slide clamps used with parenteral administration sets is that they do not remain at a selected point on the tubing length when in the full-flow, or on, position. Thus, when a nurse or other operator desires to employ the clamp to occlude the tubing lumen, he or she must take the time to search for the slide clamp, which is usually of relatively small dimensions and difficult to locate immediately on the administration set. This is especially so when the administration set, as is often the case, includes many other elements, such as roller clamps, injection sites, filter housings, check valves, drip chambers and the like.

The administration set is usually disposed substantially vertically, between a solution container at its upper end and a patient's arm or other venous access site at the lower end. Thus, as the administration set is set up between the solution source and the patient, a slide clamp on the tubing is jostled so that it falls until it rests upon one of the other elements in the administration set.

The search for the slide clamp is time consuming and bothersome. Once found, the operator will move the slide clamp along the length of tubing to an elevation which does not interfere with any other set element and which is also convenient for use by the operator. Once this is done, the operator will close the slide clamp. However, the slide clamp will usually be reemployed by sliding it along its slot from the lumen occluding "off mode" back to the on mode. When the slide clamp is readjusted to the on mode, it will once again slide down the tubing, making necessary a still subsequent search if it is to be used again.

Attempts have been made to solve this problem, as shown in U.S. Pat. No. 2,889,848 to Redmer. Redmer employs a two piece structure including a slide-type clamp, in conjunction with a clamp body section or block. The Redmer clamp is designed for being maintained at a given elevation while in the on position by carefully dimensioning the block bore to the tubing diameter. Thus, the Redmer clamp may be used with essentially only one tubing size. Also, the Redmer clamp is relatively expensive to manufacture. One of the key advantages of slide clamps is that they are inexpensive. If the cost of a slide clamp is too great, other devices, such as roller clamps, can easily be used.

Another disadvantage of known slide clamps is that they must be installed on the administration set during manufacture, as opposed to being added by a nurse or other operator during use. The clamp shown in Redmer may be added at the time of use but necessitates keeping track of two separate pieces and suffers from the other disadvantages discussed above.

SUMMARY OF THE INVENTION

The slide clamp of the present invention solves all of the above problems. The slide clamp is of simple construction and inexpensive to manufacture. It may be selectively positioned and maintained at any point along a length of flexible tubing while the slide clamp is in the open, or on mode. While maintaining its position at any elevation, the slide clamp is still easily moved along the length of tubing without overcoming a strong interference fit between the slide clamp and tubing.

The slide clamp of the present invention includes a platform having first and second ends and a slot through the platform extending generally between the first and second ends. The slot includes a receiving portion near the first end. When the tubing is disposed in the receiving portion, the tubing lumen is not restricted or not significantly restricted, thereby enabling a full-flow, or on mode. The slot narrows from the receiving portion to a crimping portion dimensioned to severely restrict the tubing lumen, thereby preventing or severely limiting fluid flow.

In accordance with the invention, the slide clamp includes a clamp stabilizer projecting from the platform into the receiving portion of the slot at the first end side of the receiving portion. The stabilizer includes a base at the end of the receiving portion and narrows to a tip opposite the base.

The distance between the first and second ends of the platform is substantially greater than the thickness of the platform so as to make sliding of the clamp along the tubing length easy and to maintain the tubing in a substantially vertical position. The receiving portion, with the stabilizer tip projecting thereinto, is dimensioned so as to be freely slidable along the tubing length when the clamp is held in a substantially horizontal position or, more generally, when held substantially orthogonal to the tubing length.

In the preferred embodiment the slide clamp also includes a channel extending from the first end to the stabilizer tip, thereby substantially bisecting the stabilizer, allowing for flexure of the two formed legs of the platform to facilitate the selective positioning of the clamp on the tubing length. The channel also allows the clamp to be added to the administration set tubing at the time of use, while the stabilizer halves aid in preventing inadvertent disengagement of the slide clamp from the tubing.

BRIEF DESCRIPTION OF THE DRAWINGS

FIG. 1 is a perspective view of the slide clamp of the invention in the full-flow, or on, position.

FIG. 2 is a top plan view of the slide clamp.

FIG. 3 is an enlarged fragmentary top plan view of the slide clamp.

FIG. 4 is a perspective view illustrating selective positioning of the slide clamp along the tubing length.

FIG. 5 is a perspective view of the slide clamp in the no-flow, or off, position.

FIG. 6 is a cross-sectional view, taken at line 6—6 of FIG. 6.

FIG. 7 is a top plan view of an alternate embodiment of the invention.

DETAILED DESCRIPTION OF THE PREFERRED EMBODIMENT

The present invention is embodied in a slide clamp 10 which may be selectively positioned and maintained at any point or elevation along a length of flexible tubing such as parenteral administration set tubing, while the clamp is in the full-flow or on mode. By keeping the slide clamp in a given position, the operator saves time and can more easily operate the slide clamp. The slide clamp 10 includes a stabilizer 24 which facilitates the selective positioning of the slide clamp at a desired elevation without significantly restricting the tubing lumen and while still providing for easy selective movement of the slide clamp along the tubing length.

More particularly, referring to FIGS. 1 through 6, the slide clamp 10 includes a platform 16 which in the preferred embodiment includes a border 17, such as shown in U.S. Pat. No. 4,248,401 incorporated by reference herein, which is of somewhat greater thickness than the platform 16, extending both above and below the platform. The platform 16 defines a slot 18. The slot includes defined tubing receiving and tubing crimping portions 20, 22, respectively. The slot preferably gradually narrows from the receiving portion 20 to the crimping portion 22. The slot is entirely through the platform 16 from the top side 32 to the bottom side 34 and extends generally between the first and second ends 36, 38, respectively, of the platform 16. The receiving portion 20 is disposed near the first end 36.

The slide clamp 10 includes a clamp stabilizer 24 projecting into the receiving portion 20 of the slot 18 at a first end side 40 of the receiving portion 20. The stabilizer includes a base 26 at the first end side 40 of the receiving portion 20 and narrows to a tip 28 at the distal end of the stabilizer 24.

In the preferred embodiment of the invention, the slide clamp 10 includes a channel 42 through the platform 16, extending from the first end 36 to the stabilizer tip 28. The channel 42 bisects the stabilizer 24 into stabilizer halves 24a, 24b and tip halves 28a, 28b and defines two legs 44a, 44b in the platform 16. Each of the stabilizer halves 24a, 24b is integral with its associated leg 44a, 44b, respectively. The legs 44a, 44b, with the stabilizer halves 24a, 24b extending inwardly therefrom, are capable of flexure toward and away from each other, thus aiding in mounting the slide clamp 10 about the tubing 14 through the channel 42 and also facilitating the selective positioning of the slide clamp 10 at any selected elevation on the tubing 14.

The slide clamp 10 may be easily and inexpensively manufactured from plastic. Samples have been made of P.E.T.G., (glycol modified polyethylene terephthalate), a copolyester, which works well. It is possible that other materials will also work.

In the preferred embodiment the slide clamp 10 is elongated but this is not necessary; the top and bottom sides 32, 34 may, for example, define a square shape. The distance between the first end 36 and the stabilizer tip 28 is not greater than about one third the distance betwen the first and second ends 36, 38. The ratio of the distance between the tip 28 and the first end 36 to the distance between the first and second ends 36, 38 is important in maintaining the slide clamp at a given elevation in the on mode as seen, for example, in FIG. 1. The greater distance between the tip 28 and the second end 38 as compared to the distance between the tip 28 and the first end 36 will bias the clamp 10 so that the stabilizer 24 extends downwardly from the base 26 to the tip 28 when the clamp is in the on position, mounted about the tubing.

Also, in the preferred embodiment, the distance between the first and second ends 36, 38 is substantially greater than the thickness of the platform 16 between the top and bottom sides 32, 34. By making the slide clamp 10 relatively thin, it may be more easily moved along the tubing length and does not tend to bend the tubing from its vertical position when the clamp is in the on mode.

The clamp may be mounted about the tubing by either threading the tubing through the receiving portion 20 during manufacture or else by sliding the tubing 14 through the channel 42 into the receiving portion 20. A widened, angled channel entry 42a aids in urging the tubing through the channel. After the administration set is hung from a solution container so that the tubing 14 is substantially vertical, the slide clamp 10 will be maintained at one elevation as seen in FIG. 1. The tubing 14 will be trapped between the stabilizer tip 28 and wall segments 46, 48 of the slot 18 in the receiving portion 20, which segments generally face the stabilizer tip 28.

Since the stabilizer tip 28 and receiving portion 20 are near the first end of the slide clamp 10, the second end 38 will be weighted and stay at a lower elevation than the first end 36. Since the slide clamp is disposed at an angle relative to the vertical tubing 14, the area defined between the wall segments 46, 48 and the stabilizer tip 28 is decreased along a horizontal plane. Because the slide clamp is relatively light in weight and thin, the tubing 14 remains substantially vertical and the tubing lumen 12 is not affected or is not significantly restricted. The configuration of the tubing cross-section remains unchanged. Fluid may freely flow through the lumen 12 at the slide clamp 10. The tip 28 is relatively small so that the area of surface contact with the tubing is small. Each of the tip halves 28a, 28b is rounded to prevent any possibility of puncturing the tubing.

Such a design enables a slide clamp 10 of particular dimensions to be employed as an elevation-selective clamp with a relatively wide range of medical tubing sizes. For example, in one embodiment the length (dimension A) of the slide clamp is about 1.50 in. and the width (dimension B) of the slide clamp is about 0.525 in. The slide clamp 10 may be used with tubing 14 having an outer diameter as small as about 0.13 in. and as large as about 0.18 in. Other dimensions of the clamp, with reference characters to the drawing, are as follows:

Channel Length (C): About 0.32 in.
Channel Width (D): About 0.02 in.
Receiving Portion Length (E): About 0.42 in.
Receiving Portion Width at Widest Point (F): About 0.20 in.
Crimping Portion Length (G): About 0.49 in.
Crimping Portion Width (H): About 0.02 in.
Platform Thickness (I): About 0.06 in.
Border Thickness (J): About 0.16 in.

The slide clamp 10 is moved from the on position to the off position shown in FIG. 5 in the normal manner, i.e., the slide clamp 10 is manually urged against the tubing so that the tubing enters the crimping portion 22.

To change the elevation of the slide clamp 10, the tubing 14 is placed in the receiving portion 20. The second end 38 of the clamp 10 is grasped by the operator so that the clamp and tubing length 14 are mutually orthogonal, as seen in FIG. 4. In the usual case, this means that the slide clamp will be held in a substantially horizontal plane. The slide clamp 10 is then raised or lowered to the desired elevation and released. The clamp 10 will regain its angled position relative to the tubing 14, as shown in FIG. 1, and the tip halves 28a, 28b of the stabilizer 24 will prevent the clamp 10 from sliding down the tubing 14. Additionally, the stabilizer halves 24a, 24b prevent inadvertent removal of the clamp 10 from the tubing 14 through the channel 42.

In FIG. 7 there is shown a slide clamp 50 in accordance with an alternate embodiment of the invention. The slide clamp 50 does not include a channel 42 so that the stabilizer 52 is not split. It is believed that the embodiment shown in FIG. 7 will achieve the principal goal of the present invention, which is to make the slide clamp selectively positionable and maintainable at any elevation on flexible tubing in the full-flow position. However, the flexure capability of the legs 44a, 44b and the associated stabilizer halves 24a, 24b present in the slide clamp 10 of FIGS. 1 through 6 is not present in the slide clamp 50. It is believed that the slide clamp 50 may have a decreased ability to maintain the tubing 14 at a selected height in the on position.

While various features and embodiments have been described in detail herein and shown in the accompanying drawings, it will be evident that various further modifications are possible without departing from the scope of the invention.

What is claimed is:

1. A slide clamp comprising:
   (a) a platform including first and second ends;
   (b) a defined slot through said platform, extending generally between said first and second ends of said platform, said slot including a defined tubing receiving portion near said first end, dimensioned so as not to significantly restrict the lumen of tubing disposed therein, thereby forming an on mode, said receiving portion narrowing to a defined tubing crimping portion dimensioned to severely restrict the lumen of tubing disposed therein, thereby forming an off mode, wherein said clamp is manually adjustable on the tubing between said receiving and crimping portions; and
   (c) a clamp stabilizer projecting from said platform into said receiving portion of said slot at a first end side of said receiving portion, said stabilizer including a base at said first end side and narrowing to a tip at its distal end, opposite said base;
   (d) wherein the distance between said first and second ends is substantially greater than the thickness of said platform and further wherein the distance between said first end and said stabilizer tip is not greater than about one third the distance between said first and second ends;
   (e) such that said slide clamp is selectively positionable and maintainable at any elevation along the length of the tubing while said slide clamp is in the on mode.

2. The slide clamp as in claim 1, further including a channel through said platform, extending from said first end to said stabilizer tip, so that said platform includes two legs and so as to substantially bisect said stabilizer, such that said stabilizer includes two halves and two stabilizer tip halves, each of said stabilizer halves being integral with its associated leg wherein said legs, with the associated stabilizer halves thereon, are capable of flexure toward and away from each other when the tubing is disposed within said receiving portion of said slide clamp.

3. The slide clamp as in claim 2, wherein said slide clamp may be mounted about a length of tubing by urging the tubing through said channel into said receiving portion.

4. The slide clamp as in claim 2, wherein said stabilizer halves prevent inadvertent removal of said slide clamp from the tubing, through said channel.

5. The slide clamp as in claim 1, such that when the tubing is disposed in said receiving portion said slide clamp does not change the configuration of the tubing cross-section.

6. The slide clamp as in claim 1, wherein said platform is a plastic material.

7. A slide clamp for flexible tubing, comprising:
   (a) a platform including first and second ends;
   (b) a defined slot through said platform extending generally between said first and second ends of said platform, said slot including a defined tubing receiving portion near said first end, dimensioned so as not to significantly restrict the lumen of tubing disposed therein, said receiving portion narrowing to a defined tubing crimping portion dimensioned to severely restrict the lumen of tubing disposed therein; and
   (c) a clamp stabilizer projecting from said platform into said receiving portion of said slot at a first end side of said receiving portion, said stabilizer including a base at said first end side and narrowing to a tip at its distal end, opposite said base,
   wherein said stabilizer is substantially bisected by a channel through said platform extending from said first end to said stabilizer tip so that said stabilizer comprises two halves, including two stabilizer tip halves, each of said stabilizer halves being capable of flexure toward and away from each other when the tubing is disposed within said receiving portion of said slide clamp,
   wherein the distance between said first end and said stabilizer tip is not greater than about one third the distance between said first and second ends, and
   wherein the distance between said first and second ends is substantially greater than the thickness of said platform;
   (d) such that such slide clamp is manually adjustable on the tubing between said receiving and crimping portions and is selectively positionable and maintainable at any elevation along the length of the tubing when the tubing is disposed within said receiving portion.

* * * * *